(12) United States Patent
Bovy et al.

(10) Patent No.: US 6,617,336 B1
(45) Date of Patent: Sep. 9, 2003

(54) 2-ARYLQUINOLINE DERIVATIVES, PREPARATION AND THERAPEUTIC USE THEREOF

(75) Inventors: Philippe R Bovy, Mareil Marly (BG); Alain Braun, Boulogne Billancourt (FR); Christophe Philippo, Rueil-Malmaison (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/130,875

(22) PCT Filed: Nov. 21, 2000

(86) PCT No.: PCT/FR00/03224
§ 371 (c)(1),
(2), (4) Date: May 22, 2002

(87) PCT Pub. No.: WO01/38310
PCT Pub. Date: May 31, 2001

(30) Foreign Application Priority Data

Nov. 25, 1999 (FR) ............................................. 99 14817

(51) Int. Cl.$^7$ ................... A61K 31/4706; C07D 215/16
(52) U.S. Cl. ...................... 514/314; 546/173; 546/176; 514/311; 514/314
(58) Field of Search ............................... 546/176, 173; 514/311, 314

(56) References Cited

U.S. PATENT DOCUMENTS

| | | | |
|---|---|---|---|
| 6,060,508 A | 5/2000 | Philippo et al. | 514/469 |
| 6,063,810 A | 5/2000 | Philippo et al. | 514/469 |
| 6,331,549 B1 * | 12/2001 | Philippo et al. | 514/311 |

FOREIGN PATENT DOCUMENTS

| | | |
|---|---|---|
| FR | 2 752 840 | 3/1998 |
| FR | 2 756 564 | 6/1998 |
| FR | 2 785 903 | 5/2000 |
| WO | WO 97 32870 A | 9/1997 |
| WO | WO 98 08834 A | 3/1998 |

OTHER PUBLICATIONS

Derwent Patent Abstract No. 199817.
Derwent Patent Abstract No. 199829.
Derwent Patent Abstract No. 200033.

* cited by examiner

Primary Examiner—Alan L. Rotman
Assistant Examiner—Janet L Coppins
(74) Attorney, Agent, or Firm—Paul E. Dupont; Michael D. Alexander

(57) ABSTRACT

Compounds of general formula (I)

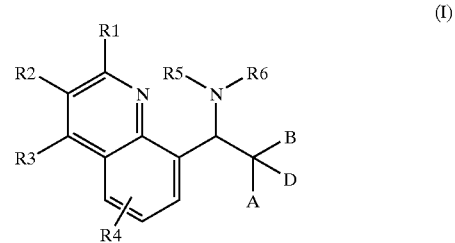

in which:

A represents a hydrogen atom, a hydroxyl, a $C_{1-3}$ alkoxy group, a hydroxy($C_{1-6}$ alkyl) group, a ($C_{1-3}$ alkoxy)($C_{1-3}$ alkyl) group, a thiol, ($C_{1-6}$ alkyl)sulfanyl or a halogen;

B and D represent, independently of one another, a hydrogen atom, a $C_{1-6}$ alkyl group, a fluoro($C_{1-6}$ alkyl) group or a perfluoro($C_{1-2}$ alkyl) group or B and D together from an oxo;

$R_1$ represents a phenyl, a naphthyl or a heteroaryl comprising 4 or 5 carbon atoms;

$R_2$ and $R_3$ represent, independently of one another, a hydrogen atom, a halogen or a $C_{1-6}$ alkyl group, $R_4$ represents a hydrogen atom, a hydroxyl or a halogen, and $R_5$ and $R_6$ represent, independently of one another, a hydrogen atom, a $C_{1-6}$ alkyl group, a $C_{2-6}$ alkenyl group, a $C_{3-6}$ cycloalkyl group, a $C_{3-6}$ cycloalkenyl group, a fluoro($C_{1-6}$ alkyl) group or a perfluoro($C_{1-2}$ alkyl) group or $R_5$ and $R_6$ together form a $C_{2-6}$ alkylene chain or a $C_{3-6}$ alkenylene chain, to give, with the nitrogen to which they are attached, a heterocycle, this heterocycle optionally being substituted by a $C_{1-4}$ alkyl group; and their salts.

18 Claims, No Drawings

2-ARYLQUINOLINE DERIVATIVES, PREPARATION AND THERAPEUTIC USE THEREOF

The subject matter of the invention is 2-arylquinoline derivatives, their preparation and their application in therapeutics.

The compounds correspond to the general formula (I)

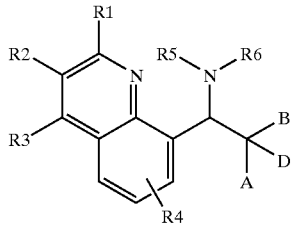

in which:
- A represents a hydrogen atom, a hydroxyl, a $C_{1-3}$ alkoxy group, a hydroxy($C_{1-6}$ alkyl) group, a ($C_{1-3}$ alkoxy)($C_{1-3}$ alkyl) group, a thiol, ($C_{1-6}$ alkyl)sulfanyl or a halogen;
- B and D represent, independently of one another, a hydrogen atom, a $C_{1-6}$ alkyl group, a fluoro($C_{1-6}$ alkyl) group or a perfluoro($C_{1-2}$ alkyl) group or B and D together from an oxo;
- $R_1$ represents a phenyl, a naphthyl or a heteroaryl comprising 4 or 5 carbon atoms and, as heteroatom, an oxygen, a sulfur or a nitrogen; it being possible for the phenyl, the naphthyl or the heteroaryl to be substituted by one, two or three substituents chosen from the group consisting of a halogen, a hydroxyl, a nitro, an amino, an azido, a $C_{1-6}$ alkyl group, a hydroxy($C_{1-6}$ alkyl) group, a ($C_{1-6}$ alkyl)carbonyl group, a ($C_{1-6}$ alkyl) amino group, a di($C_{1-6}$ alkyl)amino group, a fluoro ($C_{1-6}$ alkyl) group, a perfluoro($C_{1-2}$ alkyl) group, a $C_{1-6}$ alkoxy group, a phenyl and a benzyl, and a benzyloxy;
- $R_2$ and $R_3$ represent, independently of one another, a hydrogen atom, a halogen or a $C_{1-6}$ alkyl group,
- $R_4$ represents a hydrogen atom, a hydroxyl or a halogen, and
- $R_5$ and $R_6$ represent, independently of one another, a hydrogen atom, a $C_{1-6}$ alkyl group, a $C_{2-6}$ alkenyl group, a $C_{3-6}$ cycloalkyl group, a $C_{3-6}$ cycloalkenyl group, a fluoro($C_{1-6}$ alkyl) group or a perfluoro($C_{1-2}$ alkyl) group or $R_5$ and $R_6$ together form a $C_{2-6}$ alkylene chain or a $C_{3-6}$ alkenylene chain, to give, with the nitrogen to which they are attached, a heterocycle, such as, for example, a piperidyl, azetidinyl or pyrrolidyl, this heterocycle optionally being substituted by a $C_{1-4}$ alkyl group; and their salts.

The preferred compounds according to the invention are chosen from the following subgroups, in which:
- A represents a hydrogen, hydroxyl, a thiol or a halogen and more particularly a hydroxyl; and/or
- B and D represent a hydrogen atom; and/or
- $R_1$ represents a phenyl, a naphthyl or a heteroaryl comprising 4 or 5 carbon atoms and, as heteroatom, a sulfur or a nitrogen, it being possible for the phenyl, the naphthyl or the heteroaryl to be substituted by one, two or three substituents chosen from the group consisting of a halogen, a hydroxyl, a nitro, an amino, an azido, a $C_{1-3}$ alkyl group, a hydroxy($C_{1-3}$ alkyl) group, a ($C_{1-3}$ alkyl)carbonyl group, a ($C_{1-3}$ alkyl)amino group, a di($C_{1-3}$ alkyl)amino group, a fluoro($C_{1-6}$ alkyl) group, a perfluoro($C_{1-2}$ alkyl) group, a $C_{1-3}$ alkoxy group, a phenyl, a benzyl and a benzyloxy; and/or
- $R_2$ and $R_3$ represent, independently of one another, a hydrogen atom or a $C_{1-6}$ alkyl group, more particularly a $C_{1-3}$ alkyl group; and/or
- $R_5$ and $R_6$ represent, independently of one another, a hydrogen atom or a $C_{1-6}$ alkyl group, more particularly a $C_{1-3}$ alkyl group, or $R_5$ and $R_6$ together form a $C_{2-6}$ alkylene chain, to give, with the nitrogen to which they are attached, a heterocycle, such as, for example, a piperidyl, azetidinyl or pyrrolidyl, more particularly piperidyl, this heterocycle optionally being substituted by a $C_{1-4}$ alkyl group, more particularly a $C_{1-2}$ alkyl group.

A particularly preferred subgroup of compounds of formula (I) is that in which A, B, D, $R_1$, $R_2$, $R_3$, $R_5$ and $R_6$ are as defined above in the subgroups of preferred compounds and $R_4$ is as defined above.

In particular, the following subgroup of compounds is particularly preferred:
- A represents a hydroxyl,
- B and D and $R_4$ represent a hydrogen atom,
- $R_1$ represents a naphthyl, a thiophene, a pyridine or a phenyl, it being possible for the phenyl to be substituted by one, two or three substituents chosen from the group consisting of a a halogen, a hydroxyl, a nitro, an amino, an azido, a $C_{1-3}$ alkyl group, a hydroxy($C_{1-3}$ alkyl) group, a ($C_{1-3}$ alkyl)carbonyl group, a ($C_{1-3}$ dialkyl) amino group, a perfluoro($C_{1-2}$ alkyl) group, a $C_{1-3}$ alkoxy group, a phenyl and a benzyloxy,
- $R_2$ and $R_3$ represent, independently of one another, a hydrogen atom or a $C_{1-3}$ alkyl group, and
- $R_5$ and $R_6$ represent, independently of one another, a $C_{1-3}$ alkyl group or $R_5$ and $R_6$, together with the nitrogen to which they are attached, a piperidyl, this piperidyl optionally being substituted a $C_{1-2}$ alkyl group.

The preferred compounds are shown in the table below; mention may more particularly be made of the following compounds:
- 2-Phenyl-3-methyl-8-(1-diethylamino-2-hydroxyethyl) quinoline,
- 2-Phenyl-3-methyl-8-(1-(R)-[2'-(R)methylpiperidino]-2-hydroxyethyl)quinoline,
- 2-Phenyl-8-(1-diethylamino-2-hydroxyethyl)quinoline,
- 2-Thiophen-2-yl-8-(1-diethylamino-2-hydroxyethyl) quinoline, and
- 2-(2-Fluorophenyl)-3-methyl-8-(1-diethylamino-2-hydroxyethyl)quinoline.

In the present application:
- $C_{1-z}$ (or $C_{2-z}$ or $C_{3-z}$), where z can take the values between 2 and 6, represents a carbonaceous chain which can have from 1 (or 2 or 3) to z carbon atoms,
- the term alkyl, alkenyl or alkoxy respectively represents an alkyl, alkenyl or alkoxy with a linear or branched carbonaceous chain,
- the term alkylene or alkenylene respectively represents a divalent alkyl or alkenyl with a linear or branched carbonaceous chain,
- the term heteroaryl represents an aromatic ring comprising 4 or 5 carbon atoms and a heteroatom; such a ring is, for example, a thiophene, a furan or a pyridine,
- Pg represents a protective group; examples of protective groups and protection and deprotection methods are given in *Protective Groups in Organic Synthesis*, Greene et al., 2nd Ed. (John Wiley & Sons Inc., New York), and
- halogen represents an iodine, bromine, chlorine or fluorine atom.

The compounds of general formula (I) can comprise one or more asymmetric carbon atoms. They can therefore exist in the form of enantiomers or of diastereoisomers. These enantiomers and diastereoisomers, and their mixtures, including racemic mixtures, form part of the invention.

When a compound according to the invention exhibits stereoisomerism, for example of axial-equatorial or Z-E type, the invention comprises all the stereoisomers of these compounds.

The compounds of general formula (I) can be provided in the form of the free base or in the form of addition salts with acids, which also form part of the invention. These salts, according to the present invention, comprise those with inorganic or organic acids which make possible suitable separation or crystallization of the compounds of formula (I), such as picric acid, oxalic acid or an optically active acid, for example a tartaric acid, a dibenzoyltartaric acid, a mandelic acid or a camphorsulfonic acid, and those which form physiologically acceptable salts, such as the hydrochloride, hydrobromide, sulfate, hydrogensulfate, dihydrogenphosphate, maleate, pamoate, fumarate, 2-naphthalenesulfonate or para-toluenesulfonate. Even if the pharmaceutically acceptable salts are preferred, the other salts form part of the present invention. These salts can be prepared according to methods known to a person skilled in the art, for example by reaction of the base with the acid in an appropriate solvent, such as an alcoholic solution or an organic solvent, and then separation from the medium in which they are present by evaporation of the solvent or by filtration.

The compounds of the invention can be prepared by processes illustrated by the schemes which follow.

The compounds of formula (I), in particular those for which A represents hydroxyl, can be prepared according to the process described in scheme 1.

catalyzed Stille coupling with a compound of formula VI, under the conditions defined by McKean, D. R.; Parinello, G.; Renaldo, A. F.; Stille, J. K., J. Org. Chem., 52, 1987, 492, to give an ethenyl derivative of formula IV.

The ethenyl derivative of formula IV thus obtained is reacted with an oxidizing agent, such as sodium periodate, osmium tetroxide or meta-chloroperbenzoic acid, followed by hydrolysis in a basic or acidic medium, according to conventional methods known to a person skilled in the art, to form a diol of formula III. It is also possible to use AD-mix to obtain asymmetric hydroxylation in an alcoholic solvent, such as, for example, a mixture of tert-butanol in the presence of water, at a temperature preferably of between −10° C. and 5° C.

The hydroxyl group geminal to the B group of the compound of formula III is selectively protected by a protective group Pg according to methods known to a person skilled in the art, for example by formation of a silyl ether, such as, for example, the tert-butydinethylsilyl ether, so as to obtain the compound of formula II in which Pg represents a protective group. The hydroxyl group carried by the carbon alpha to the quinoline of the compound of formula II thus obtained can subsequently be optionally activated, in a way known to a person skilled in the art, so as to obtain a nucleofuge group, such as a mesyl group, a tosyl or a bromine atom.

The compound of formula (I) according to the invention is subsequently prepared from the latter compound by reacting it with an amine $NHR_5R_6$. This reaction can be carried out in an aprotic organic solvent, such as chloroform or methylene chloride, at a temperature between ambient temperature and the reflux temperature of the solvent, in the presence of an excess of amine (from 0.2 to 100 equivalents in excess).

The compound is subsequently deprotected according to methods known to a person skilled in the art to give the

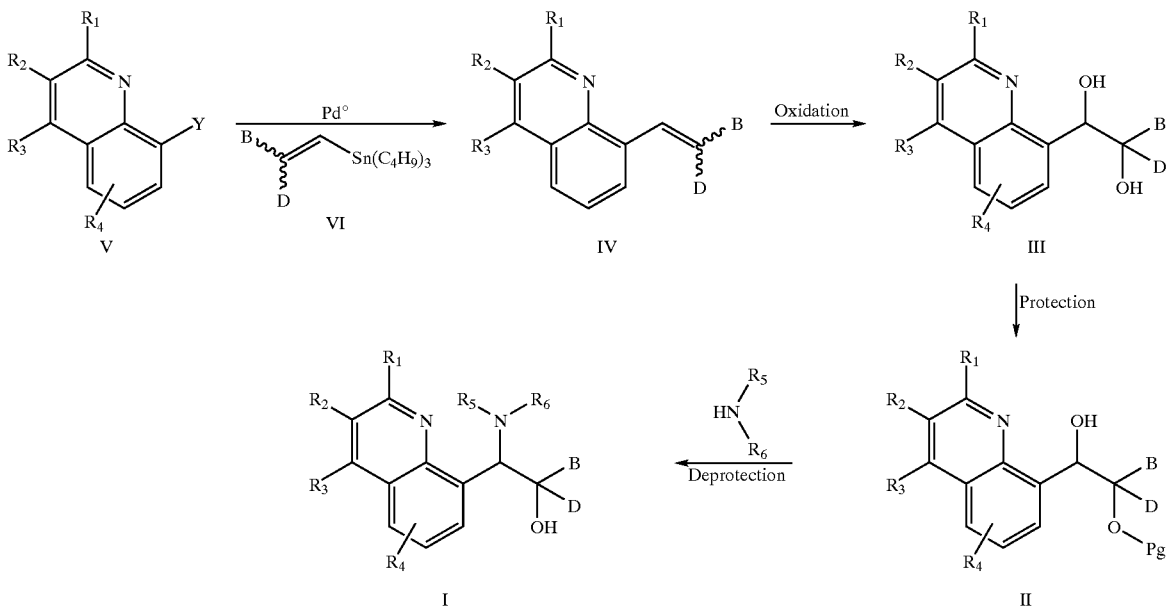

According to this process, a quinoline derivative of formula V, in which Y represents a nucleofuge group, such as a halogen or an activated hydroxyl group, for example activated in the triflate form, is reacted by palladium-catalyzed compound of formula (I). The meanings of $R_1$, $R_2$, $R_3$, $R_4$, $R_5$, $R_6$ and B in each of the compounds of formulae II, III, IV, V and VI and of the amine $NHR_5R_6$ are those indicted for the formula (I).

The compound of formula V and also the compound of formula IV can be prepared according to methods disclosed in PCT/FR99/02129 and French application No. 9814389.

Alternatively, it is possible to prepare the compounds of formula V according to the methods described below.

Thus, the compounds of formula V can be prepared either by a Skraup or Doebner-Miller reaction, according to reaction scheme 2.

Scheme 2

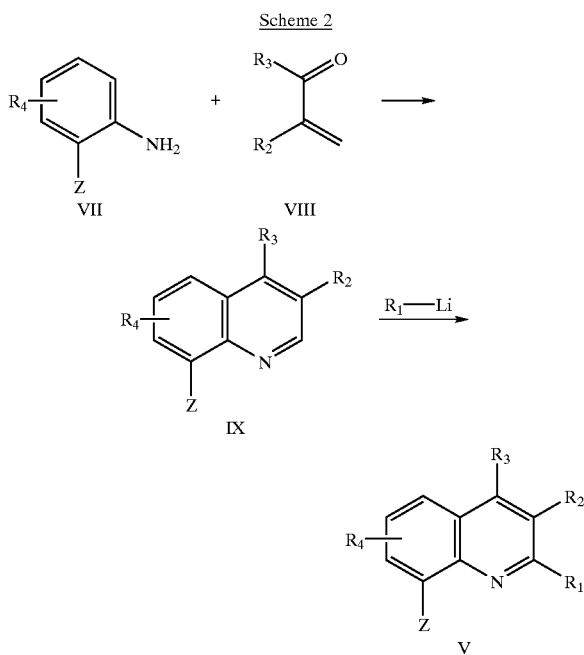

According to this process and under the conditions defined by Belser P. (Tetrahedron, 1996, vol. 52, No. 8, 2937–2944) or advantageously under the conditions defined by Z. Song J. (Heterocyclic Chem., 1993, 30, 17–21), an aniline of formula VII, for which Z represents a hydroxyl or methoxy group, and an α,β-unsaturated aldehyde or an α,β-unsaturated ketone formula VIII are heated in the presence of a dehydrating agent, such as sulfuric acid, and of an oxidizing agent, such as sodium iodide, to form a quinoline derivative, substituted in the 8 position by Z, of formula IX. This compound is then treated with an aryllithium (or heteroaryllithium) derivative, denoted by $R_1$—Li, in a solvent, such as toluene, to give a compound of formula V.

The meanings of $R_1$, $R_2$, $R_3$ and $R_4$ of the compounds of formula V, VII, VIII and IX are those indicated in the formula I.

The compounds of formula V can also be prepared by a Friedländer condensation reaction reaction scheme 3.

Scheme 3

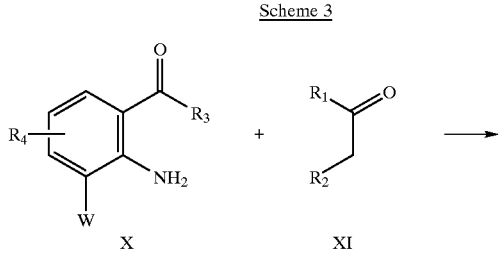

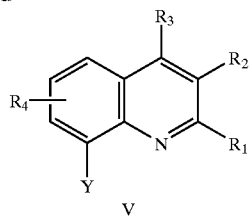

According to this process and under the conditions defined by R. P. Thummel et al. (J. Org. Chem., 1993, 58, 1666–1671), an aryl (or heteroaryl) ketone of formula XI is reacted with a 2-acylaniline of formula X, in which W represents a halogen, such as iodine, bromine or chlorine, or a hydroxyl or methoxy group, in a solvent with a high boiling point, such as toluene, in the presence of alcoholic potassium hydroxide. In the case where W is a hydroxyl or methoxy, this reaction is followed by the conversion of these groups into the leaving group Y as defined above, according to methods known to a person skilled in the art, to give the compounds of formula V. For example, in the case where W is a methoxy, the latter is converted first into a hydroxyl, by the action of boron tribromide in a solvent, such as dichloromethane or chloroform, at a temperature preferably of −30° C. to 0° C. The hydroxyl is subsequently converted into a leaving group, for example by the action of trifluoromethanesulfonic anhydride in a solvent, such as pyridine, at temperatures preferably of between −10° C. and 5° C.

The meanings of $R_1$, $R_2$, $R_3$ and $R_4$ of the compounds of formula V, X and XI are those indicated in the formula (I).

Moreover, the compounds of formula (I), in particular those for which A represents a hydroxyl group, can also be prepared, according to scheme 4, from a quinoline derivative of formula XII, for which Y is as defined above, by a palladium-catalyzed Stille or Suzuki coupling (Chem. Rev., 1995, 95, 2457–2483) with a compound of formula XIII or XIV. The meanings of $R_1$, $R_2$, $R_3$, $R_4$, $R_5$ and $R_6$ of the compounds of formula XII, XIII or XIV are those indicated for the formula I.

Scheme 4

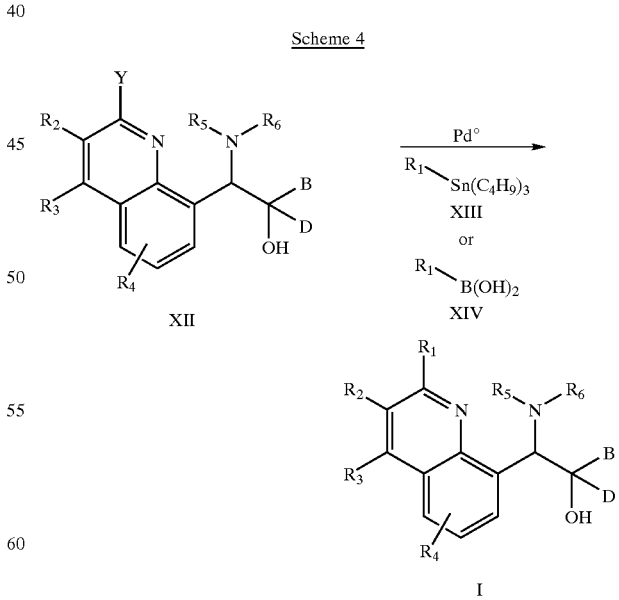

The compound of formula XII can be prepared according to the process described in scheme 5.

According to this process, a quinoline compound of formula XX is oxidized, by methods known to a person skilled in the art, to an N-oxide compound of formula XIX, which, in the presence of acetic anhydride and under the conditions defined in the patent of Tzeng, C. et al., U.S. Pat. No. 5,646,164, rearranges into a 2-acetoxyquinoline compound of formula XVIII. The hydroxyl group in the 8 position of the latter is converted to a nucleofuge group, such as a triflate group, according to methods known to a person skilled in the art, and then is brought together with a compound of formula VI by palladium-catalyzed Stille coupling, under the conditions defined by McKean, D. R. et al. (J. Org. Chem., 52, 1987, 492), to provide the ethenyl derivative of formula XVII. The acetoxy group in the 2 position of the latter derivative is subsequently converted into a Y group, representing a nucleofuge group, such as a halogen or an activated hydroxyl group, for example into a triflate, to give the ethenyl derivative of formula XVI. The quinoline derivative of formula XII can subsequently be prepared according to the reaction sequence described in scheme 1, from the quinoline of formula XVI thus obtained. The meanings of $R_2$, $R_3$, $R_4$ and B of the compounds of formula XVI, XVII, XVIII, XIX and XX are those indicated in the formula I.

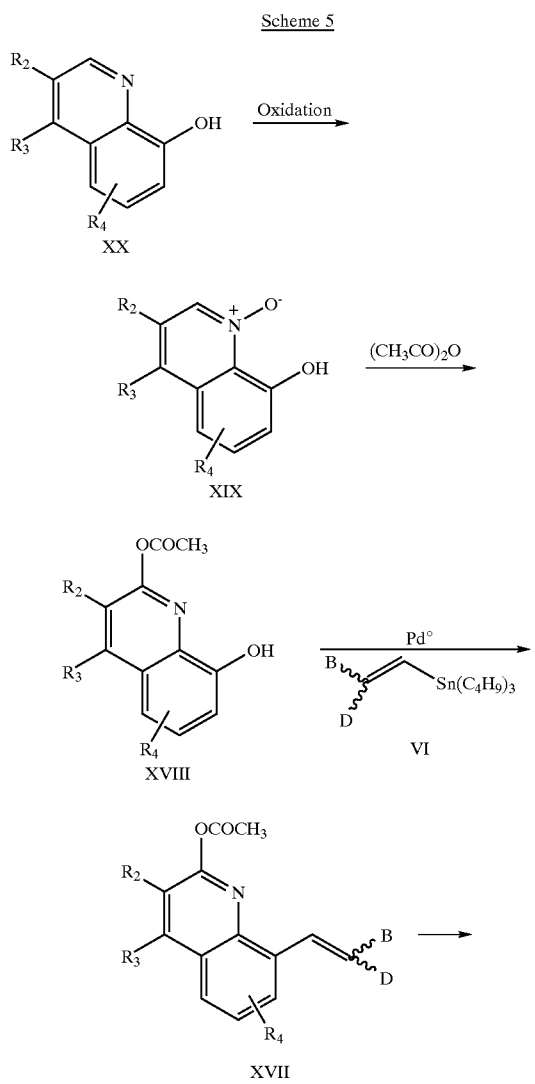

Scheme 5

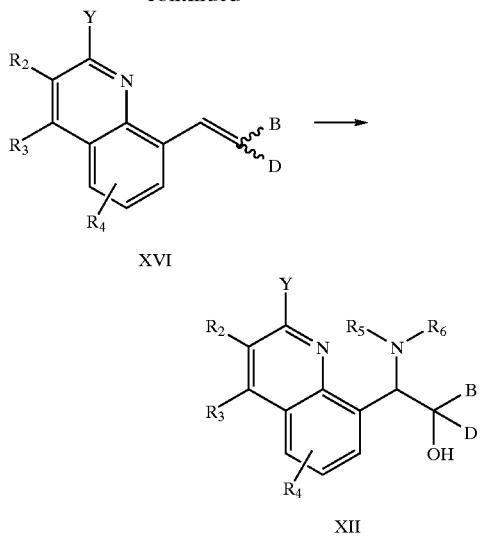

The compounds of formula (I) according to the invention in which A is not a hydroxyl group can be prepared from the compound of formula (I) where A is a hydroxyl group according to scheme 6.

According to this scheme, these compounds can be prepared from the compound of formula (I) where A is a hydroxyl group by activation of this group in a way known to a person skilled in the art, so as to obtain a nucleofuge group Y as defined above, and by then reacting the latter with a nucleophilic group XV "A". This nucleophilic group corresponding to the corresponding nucleophilic entity of the substituent A. The reaction can be carried out, for example, in a solvent, such as tetrahydrofuran, and by heating to the reflux temperature of the solvent.

Scheme 6

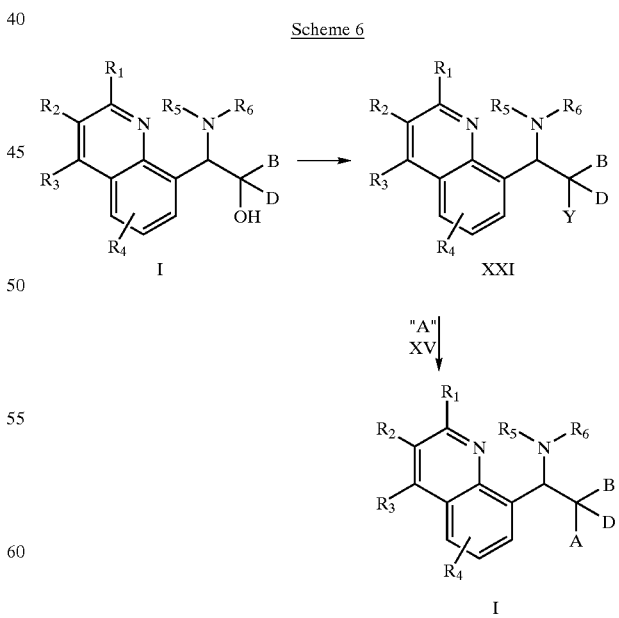

Also according to this scheme, the compounds of formula (I) according to the invention for which A is a hydrogen atom can be prepared by dehydroxylation of a corresponding compound of formula (I) where A is a hydroxyl group. The dehydroxylation reaction can be carried out in a way known to a person skilled in the art, for example by reaction with triethylsilane in trifluoroacetic acid while heating to the reflux temperature.

The compounds of formula (I) according to the invention for which A and D are hydrogen atoms can also be prepared according to the following reaction scheme 7.

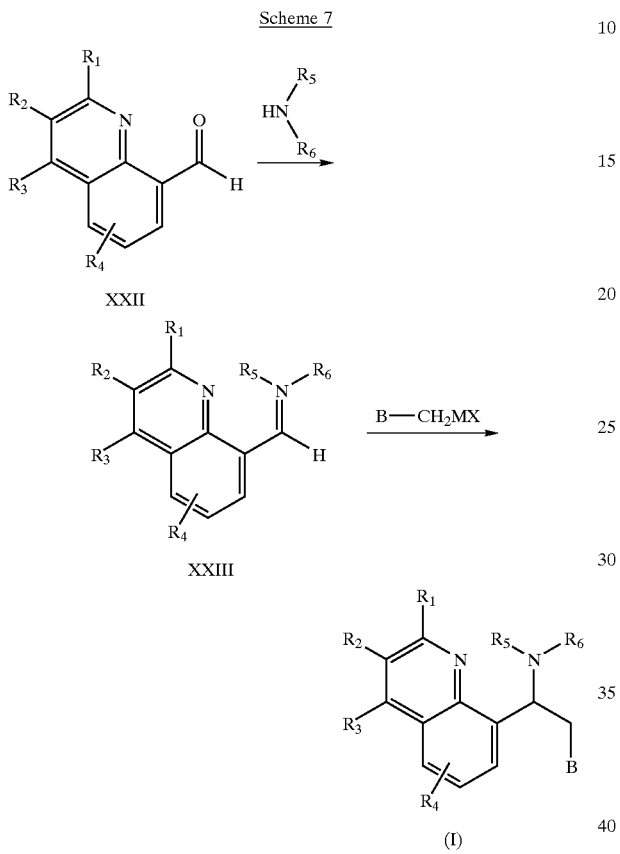

According to this process, the compound of formula (I) is prepared by reacting a nucleophilic derivative of formula B—CH$_2$MX, for which M represents a metal, X represents a halogen and B has the meaning indicated for the formula (I), such as, for example, an organomagnesium compound or an organolithium compound, with an amine derivative of formula XXIII obtained by reaction of a secondary amine of formula NHR$_5$R$_6$, for which the meanings of R$_5$ and R$_6$ are those indicated for the formula (I) with the exception of the hydrogen atom, with an aldehyde of formula XXII. The reaction can be carried out in an organic solvent, such as toluene or benzene, at reflux, with azeotropic distillation. The meanings of R$_1$, R$_2$, R$_3$, R$_4$, R$_5$, R$_6$ and B of the compounds XXII and XIII are those indicated for the formula (I).

The starting materials (VI, VII, VIII, X, XI, XIII, XIV, XX, XXII, HNR$_5$R$_6$, B—CH$_2$MX) for the syntheses of the compounds of formula (I) are directly available commercially, are known in the literature or can be synthesized by conventional methods known to a person skilled in the art.

The following examples illustrate the processes and techniques appropriate for the preparation of this invention, without, however, limiting the scope of the claim. The microanalyses and the NMR and IR spectra confirm The purpose of the following examples is to illustrate the present invention.

EXAMPLE 1

2-Phenyl-3-methyl-8-(1-(R)-[2'-(R) methylpiperidino]-2-hydroxyethyl)quinoline Hydrochloride (I): R$_1$=C$_6$H$_5$, R$_2$=CH$_3$, R$_3$=R$_4$=B=D=H, A=OH and NR$_5$R$_6$=

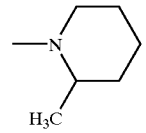

(I) 3-Methoxy-2-aminobenzaldehyde 5 g of 3-methoxy-2-nitrobenzaldehyde are dissolved in a solution of 100 ml of ethanol, 100 ml of acetic acid and 50 ml of water. After addition of 11.4 g of iron and of 1.4 ml of concentrated hydrochloric acid, the reaction medium is heated at reflux for 10–15 minutes. After having cooled the reaction medium, 150 ml of water are added and the reaction mixture is extracted with 3×200 ml of dichloromethane. The organic phases are combined, washed with 500 ml of a saturated sodium hydrogencarbonate solution, dried over magnesium sulfate, filtered and evaporated under vacuum to provide 4.7 g of 3-methoxy-2-aminobenzaldehyde in the form of a colorless oil, used without purification in the following stage. (Yield: quantitative)

(2) 2-Phenyl-3-methyl-8-methoxyquinoline 15.3 g (101 mol) of 3-methoxy-2-aminobenzaldehyde and 14 ml (105 mol) of propiophenone are dissolved in 400 ml of ethanol. 1.4 g (25 mol) of potassium hydroxide are added to the reaction mixture and the latter is brought to 100° C. for 8 hours. After cooling the reaction medium, the latter is concentrated under vacuum and 200 ml of water are added. A yellow precipitate forms after a few minutes. The medium is filtered and the yellow precipitate is taken up in a mixture of 300 ml of ethyl ether and of 200 ml of a 1N hydrochloric acid solution. The aqueous phase is extracted with 2×100 ml of ethyl ether. Then, after addition of 300 ml of methylene chloride, 100 ml of a 3N sodium hydroxide solution are added to the aqueous phase. The latter is then extracted with 3×200 ml of methylene chloride. The organic phases are combined, dried over magnesium sulfate, filtered and concentrated under vacuum. 21.2 g of 2-phenyl-3-methyl-8-methoxyquinoline are obtained in the form of a pale yellow solid; M.p.=105° C. (Yield: 85%)

(3) 2-Phenyl-3-methyl-8-hydroxyquinoline 17.6 ml (180 mmol) of boron tribromide are added dropwise, at −30° C., to a solution of 21.2 g (85 mmol) of 2-phenyl-2-methyl-8-methoxyquinoline in 500 ml of methylene chloride. The cooling bath is then removed and the reaction medium is stirred for 3 hours until it has returned to ambient temperature. The reaction mixture is then poured onto ice and the medium is basified using sodium hydrogencarbonate. The medium is subsequently extracted with 3×200 ml of methylene chloride. The organic phases are combined, dried over magnesium sulfate, filtered and evaporated under vacuum. The residue is purified by silica gel chromatography (eluent: ethyl acetate/cyclohexane 3/7) to give 12.7 g of 2-phenyl-3-methyl-8-hydroxyquinoline in the form of a colorless oil. (Yield: 64%)

(4) 2-Phenyl-3-methyl-8-trifluoromethanesulfonyloxy-quinoline 16.9 ml (110 mmol) of trifluoromethane-sulfonic anhydride are added dropwise, at 0° C., to a solution of 12.5 g (53 mmol) of 2-phenyl-3-methyl-8-hydroxyquinoline in 150 ml of pyridine. The reaction mixture is then stirred for 16 hours at ambient temperature. After evaporating the pyridine, the residue is taken up in 200 ml of water and 100 ml of ethyl acetate. The aqueous phase is extracted with 2×100 ml of ethyl acetate. The organic phases are combined, dried over magnesium sulfate, filtered and concentrated under vacuum. The residue is purified by silica gel chromatography (eluent: ethyl acetate/cyclohexane 3/7) to give 17.8 g of 2-phenyl-3-methyl-8-trifluoromethanesulfonyloxyquinoline in the form of a beige solid; M.p.=85° C. (Yield: 91%)

(5) 2-Phenyl-3-methyl-8-vinylquinoline 6.3 g (150 mmol) of lithium chloride, 16.8 ml (57 mmol) of tributylvinyltin and 1.6 g (1.5 mmol) of $Pd(PPh_3)_4$ are added sequentially at ambient temperature to a solution of 17.7 g (48 mmol) of 2-phenyl-3-methyl-8-trifluoromethanesulfonyloxyquinoline in 250 ml of dioxane, degassed beforehand using a stream of nitrogen. The reaction medium is then heated at 110° C. for 16 hours. After evaporating the dioxane, the residue is taken up in 200 ml of water and 200 ml of ethyl acetate. The aqueous phase is extracted with ethyl acetate. The organic phases are combined, dried over magnesium sulfate, filtered and concentrated under vacuum. The residue is purified by silica gel chromatography (eluent: ethyl acetate/cyclohexane 3/7) to provide 11.3 g of 2-phenyl-3-methyl-8-vinylquinoline in the form of a colorless oil. (Yield: 96%)

(6) 2-Phenyl-3-methyl-8-(1-(S),2-dihydroxyethyl)quinoline 8.6 g (35 mmol) of 2-phenyl-3-methyl-8-vinylquinoline are added, at 0° C., to a suspension of 52 g of AD-mix-α in a mixture of 200 ml of distilled water and 200 ml of tert-butanol. The reaction mixture is then vigorously stirred for 16 hours at this same temperature using a mechanical stirrer. 2 g of $Na_2SO_3$ are then added. The reaction mixture is stirred for one hour and is then taken up in 200 ml of water and extracted with 3×200 ml of ethyl acetate. The organic phases are combined, dried over magnesium sulfate, filtered and concentrated under vacuum. The residue is purified by silica gel chromatography (eluent: ethyl acetate/cyclohexane 3/7) to provide 6.65 g of 2-phenyl-3-methyl-8-(1-(S),2-dihydroxyethyl)quinoline in the form of an orange-colored solid; M.p.=117° C. (Yield: 69%)

(7) 2-Phenyl-3-methyl-8-(1-(S)-hydroxy-2-[tert-butyldimethylsilyloxy]ethyl)quinoline 3.7 g (24.3 mmol) of tert-butyldimethylsilyl chloride and 3.4 g of (50 mmol) of imidazole are added at ambient temperature to a solution of 6.5 g (23.2 mmol) of 2-phenyl-3-methyl-8-(1-(S),2-dihydroxyethyl)-quinoline in 200 ml of dimethylformamide. The reaction medium is stirred for 16 hours. After addition of 200 ml of distilled water, the reaction mixture is extracted with 3×200 ml of ethyl acetate. The organic phases are combined, washed with 300 ml of distilled water, dried over magnesium sulfate, filtered and concentrated under vacuum. The residue is purified by silica gel chromatography (eluent: ethyl acetate/cyclohexane to provide 8.4 g of 2-phenyl-3-methyl-8-(1-(S)-hydroxy-2-[tert-butyldimethylsilyloxy]ethyl)quinoline in the form of a colorless oil. (Yield: 85%)

(8) 2-Phenyl-3-methyl-8-(1-(S)-methanesulfonyloxy-2-[tert-butyldimethylsilyloxy]ethyl)quinoline 2 ml (26 mmol) of mesyl chloride and 4 ml (27 mmol) of triethylamine are added sequentially, at 0° C., to a solution of 7 g (17.8 mmol) of 2-phenyl-3-methyl-8-(1-(S)-hydroxy-2-[tert-butyldimethylsilyloxy]ethyl)quinoline in 200 ml of ethyl ether. The solution rapidly turns cloudy and a white precipitate is formed. After stirring for one hour at ambient temperature, 150 ml of distilled water are added to the reaction medium and the aqueous phase is extracted with 3×200 ml of ethyl ether. The organic phases are combined, dried over magnesium sulfate, filtered and concentrated under vacuum to provide 8.4 g of 2-phenyl-3-methyl-8-(1-(S)-methanesulfonyloxy-2-[tert-butyldimethylsilyloxy]ethyl)quinoline in the form of a colorless oil, used without purification in the following stage. (Yield: quantitative)

(9) 2-Phenyl-3-methyl-8-(1-(R)-[2-(R)-methypiperidino]-2-[tert-butyldimethylsilyloxy]ethyl)quinoline A solution of 7 g (17.8 mmol) of 2-phenyl-3-methyl-8-(1-(S)-methanesulfonyloxy-2-[tert-butyldimethylsilyloxy]ethyl)quinoline 8.8 g (88 mmol) of 2-(R)-methylpiperidine in 50 ml of anhydrous chloroform is brought to 60° C. for 6 hours. The reaction mixture is concentrated under vacuum and the residue obtained is purified by silica gel chromatography (eluent: dichloromethane/methanol 9/1) to provide 3.8 g of 2-phenyl-3-methyl-8-(1-(R)-[2-(R)-methylpiperidino]-2-[tert-butyldimethylsilyloxy]ethyl)quinoline in the form of a colorless oil. (Yield: 45%)

(10) (+)-2-Phenyl-3-methyl-8-(1-(R)-[2-(R)-methylpiperidino]-2-hydroxyethyl)quinoline A solution of 0.5 g (1.05 mmol) of 2-phenyl-3-methyl-8-(1-(R)-[2-(R)-methylpiperidino]-2-[tert-butyldimethylsilyloxy]ethyl)quinoline in a mixture of 15 ml of acetic acid, 5 ml of tetrahydrofuran and 5 ml of distilled water is heated at 70° C. for 40 hours and is then poured onto an ice-cold mixture of 150 ml of ethyl ether and of 150 ml of a saturated sodium hydrogencarbonate solution. The addition of sodium hydrogencarbonate is continued until a pH of approximately 9 is obtained. The mixture is then extracted with 3×200 ml of ethyl ether. The organic phases are combined, dried over magnesium sulfate, filtered and evaporated under vacuum. The residue is purified by silica gel chromatography (eluent: dichloromethane/methanol 9/1) to provide 0.3 g of (+)-2-phenyl-3-methyl-8-(1-(R)-[2-(R)-methylpiperidino]-2-hydroxyethyl)quinoline in the form of a colorless wax. (Yield: 75%)

(11) (+)-2-Phenyl-3-methyl-8-(1-(R)-[2-(R)-methylpiperidino]-2-hydroxyethyl)quinoline hydrochloride 8.3 ml of a 0.1N hydrochloric acid solution are added to a solution of 0.3 g (0.832 mmol) of (+)-2-phenyl-3-methyl-8-(1-(R)-[2-(R)-methylpiperidino]-2-hydroxyethyl)quinoline in 3 ml of methanol. The solvents are evaporated and the salt obtained is dissolved in 10 ml of water. The solution is filtered, frozen with a bath of dry ice in acetone, and lyophilized overnight to provide 0.33 g of (+)-2-phenyl-3-methyl-8-(1-(R)-[2-(R)-methylpiperidino]-2-hydroxyethyl)quinoline hydrochloride in the form of a white solid; M.p.=68° C. (Yield: quantitative)

EXAMPLE 2

2-Phenyl-3-methyl-8-trifluoromethane sulfonyloxyquinoline Pamoate (1) 3-Methyl-8-methoxyquinoline 94 ml of concentrated sulfuric acid and 70 ml of water are placed in a 1 l triple-necked flask equipped with a mechanical stirrer. The mixture is cooled to 0° C. with an ice bath and the dropwise addition is carried out of 45 g (366 mmol) of ortho-anisidine, followed by 0.54 g of sodium iodide. The mixture is then heated with an oil bath to 115° C. and 50 ml (604 mmol) of methacrolein are added using a syringe driver at the rate of 25 ml/h. Heating is continued for 1 h after the addition. The mixture is cooled to ambient temperature and then thrown onto a mixture of ice and of sodium carbonate. Extraction is carried out with dichloromethane. The organic phases are combined, dried over magnesium sulfate, filtered and evaporated under vacuum. The residue is purified by silica gel chromatography (eluent: dichloromethane/methanol 98/2) to provide 18.7 g of 3-methyl-8-methoxyquinoline. (Yield: 29.5%)

(2) 2-Phenyl-3-methyl-8-methoxyquinoline 84 ml of anhydrous THF and 42 ml of a 2M solution of phenyllithium in hexane are placed in a 1 l triple-necked flask cooled to 0° C. with an ice bath. The reaction medium is heated to 65° C. and a solution of 12 g (69 mmol) of 3-methyl-8-methoxyquinoline in 50 ml of toluene is added dropwise. The mixture is brought to reflux for 6 h and cooled to ambient temperature, and 50 ml of ethanol are added dropwise. The mixture is concentrated under vacuum and the residue is purified by silica gel chromatography (eluent: heptane/ethyl acetate 9/1) to provide 5.9 g of 2-phenyl-3-methyl-8-methoxyquinoline. (Yield: 35%)

(3) 2-Phenyl-3-methyl-8-hydroxyquinoline 4.75 g of (19 mmol) of 2-phenyl-3-methyl-8-methoxyquinoline and 111 ml of 48% hydrobromic acid are placed in a 1 l round-bottomed flask. The mixture is brought to reflux for 18 h and cooled to ambient temperature. Sodium bicarbonate is added to basify the solution and extraction is carried out with ethyl ether. The organic phases are combined, dried over magnesium sulfate, filtered and evaporated under vacuum to provide 4.3 g of 2-phenyl-3-methyl-8-hydroxyquinoline in the form of an oil. (Yield: 77%)

(4) 2-Phenyl-3-methyl-8-trifluoromethanesulfonyloxy quinoline 6.4 ml (38 mmol) of trifluoromethanesulfonic anhydride are added dropwise, at 0° C., to a solution of 4.3 g (18.3 mmol) of 2-phenyl-3-methyl-8-hydroxyquinoline in 50 ml of pyridine. The reaction mixture is then stirred for 16 hours at ambient temperature. After evaporating the pyridine, the residue is taken up in 100 ml of water and 100 ml of ethyl acetate. The aqueous phase is extracted with 2×100 ml of ethyl acetate. The organic phases are combined, dried over magnesium sulfate, filtered and concentrated under vacuum to give 6.6 g of 2-phenyl-3-methyl-8-trifluoromethanesulfonyloxyquinoline in the form of a beige solid; M.p.=85° C. (Yield: 99%)

By using essentially the same process as that of example 1, starting from stage (5), and by using an appropriate amine in stage (8), other compound of formula (I) according to the invention was prepared.

EXAMPLE 3

2-Phenyl-8-(1-diethylamino-2-hydroxyethyl) quinoline Pamoate (I): $R_1=C_6H_5$, $R_2=R_3=R_4=B=D=H$, A=OH and $R_5=R_6=C_2H_5$ (1) 8-Hydroxyquinoline N-Oxide 59.74 g (411 mmol) of 8-hydroxyquinoline, 350 ml (822 mmol) of dichloromethane, 82.2 ml of 35% aqueous hydrogen peroxide solution and 0.52 g (2.5 mmol) of methylrhenium trioxide (MTO) are placed in a 1 l round-bottomed flask. The reaction mixture is stirred at ambient temperature (25° C.) for 24 h and then 80 ml of aqueous hydrogen peroxide solution and 0.32 g of manganese dioxide are successively added. The mixture is stirred for 1 h 30 and then separated by settling. The aqueous phase is extracted with dichloromethane (2×200 ml). The organic phases are combined, dried over sodium sulfate, filtered and concentrated under vacuum to provide 64 g of 8-hydroxyquinoline N-oxide in the form of an organe-colored solid; M.p.=112° C. (Yield: 97%)

(2) 2-Acetoxy-8-hydroxyquinoline 64 g (397 mmol) of 8-hydroxyquinoline N-oxide, 550 ml of acetic anhydride and 40 ml of acetic acid are placed in a 1 l round-bottomed flask. The reaction mixture is heated at reflux (135° C.) for 24 h, 40 ml of acetic acid are then again added and heating is continued for 1 h 30. The reaction mixture is allowed to return to ambient temperature and 400 ml of toluene are added. A precipitate appears and is filtered off. A further 400 ml of toluene are added and filtration is carried out. The precipitate is washed with 200 ml of ethyl ether and is dried in a desiccator under vacuum over phosphorus pentoxide to provide to provide 70.5 g of 2-acetoxy-8-hydroxyquinoline in the form of a brown solid. (Yield: 88%)

2-Acetoxy-8-trifluoromethanesulfonyloxyquinoline 36 g (176 mmol) of 2-acetoxy-8-hydroxyquinoline and 300 ml are placed in a 1 l round-bottomed flask. The reaction mixture is cooled with an ice bath and 62.3 ml (370 mmol) of trifluoromethanesulfonic anhydride are added dropwise and stirring is continued at 0° C. for 3 h. The reaction mixture is poured onto a mixture of 200 ml of 3M hydrochloric acid and of ice. A brown precipitate appears and is filtered off and then washed with 3×50 ml of water and is dried in a desiccator under vacuum over phosphorus pentoxide to provide to provide 56.6 g of 2-acetoxy-8-trifluoromethanesulfonyloxy-quinoline in the form of a brown solid; M.p.=90° C. (Yield: 96%)

(3) 2-Acetoxy-8-vinylquinoline 33.6 g (100 mmol) of 2-acetoxy-8-trifluoromethanesulfonyloxyquinoline, 12.7 g of LiCl (300 mmol), 34.9 g (110 mmol) of tributylvinyltin and 5.8 g of tetrakis (triphenylphosphine)palladium are placed in a 1 l round-bottomed flask containing 300 ml of dioxane degassed beforehand. The mixture is heated at reflux for 4 h, then concentrated under vacuum and hydrolyzed by the addition of 200 ml of water. The aqueous phase is extracted with ethyl acetate (4×200 ml). The organic phases are combined, dried over magnesium sulfate, filtered and concentrated under vacuum. The residue is purified by silica chromatographic column (eluent: cyclohexane/ethyl acetate 95/5) to provide a fraction comprising 2-hydroxy-8-vinylquinoline and 18.6 g of 2-acetoxy-8-vinylquinoline in the form of a yellow oil. (Yield: 87%)

(4) 2-Hydroxy-8-vinylquinoline 18.6 g (87.3 mmol) of 2-acetoxy-8-vinylquinoline, 290 ml of water and 290 ml of methanol are placed in a 1 l round-bottomed flask. The reaction mixture is heated at 55° C. for 2 h and then the methanol is evaporated under vacuum. Extraction is carried out with ethyl acetate (2×200 ml). The organic phases are combined, dried over magnesium sulfate, filtered and concentrated under vacuum to provide 15.0 g of 2-hydroxy-8-vinylquinoline in the form of a yellow solid; M.p.=96° C. (Quantitative yield)

(5) 2-Trifluoromethanesulfonyloxy-8-vinylquinoline 7.5 g (43.86 mmol) of 2-hydroxy-8-vinylquinoline, 5.32 ml of pyridine (65.78 mmol) and 100 ml of dichloromethane are placed in a 250 ml round-bottomed flask. The mixture is cooled to 0° C. with an ice bath and 11.10 ml (65.78 mmol) of trifluoromethane-sulfonic anhydride are added dropwise. Stirring is continued at 0° C. for ½ h and the reaction mixture is hydrolyzed by addition of 100 ml of water. Extraction is carried out with dichloromethane (3×150 ml). The organic phases are combined, dried over magnesium sulfate, filtered and concentrated under vacuum. The residue is purified by silica chromotypography column (eluent: heptane/dichloromethane 1/1) to provide 7.2 g of 2-trifluoromethanesulfonyloxy-8-vinylquinoline in the form of a yellow oil. (Yield: 52%)

(6) 2-Trifluoromethanesulfonyloxy-8-(1,2-dihydroxyethyl) quinoline

A solution of 2-trifluoromethanesulfonyloxy-8-vinylquinoline in 37 ml of tert-butanol and 37 ml of water is added to a suspension, cooled to 0° C. with an ice bath, of AD-mix-α in 300 ml of tert-butanol and 300 ml of water. The reaction mixture is stirred at 0° C. for 16 h and then sodium bisulfite with 300 ml of water is added. The mixture is stirred for 1 h at ambient temperature and extraction is carried out with ethyl acetate (3×200 ml). The organic phases are combined, dried over magnesium sulfate, filtered and concentrated under vacuum. The residue is purified by silica chromatographic column (eluent: cyclohexane/ethyl acetate 1/1) to provide 12.0 g of 2-trifluoromethanesulfonyloxy-8-(1,2-dihydroxyethyl)quinoline in the form of a yellow oil. (Yield: 80%)

(7) 2-Trifluoromethanesulfonyloxy-8-(1-hydroxy-2-tert-butyldimethylsilyloxyethyl)quinoline A solution of 12 g (35 mmol) of 2-trifluoromethanesulfonyloxy-8-(1,2-dihydroxyethyl)quinoline, of 5.33 g (78.3 mmol) of imidazole and of 5.63 g of tert-butyldimethylsilyl chloride in 280 ml of DMF is stirred at ambient temperature for 16 h. 800 ml of water are added and extraction is carried out with ethyl acetate (3×250 ml). The organic phases are combined, dried over magnesium sulfate, filtered and concentrated under vacuum. The residue is purified by silica chromatographic column (eluent: cyclohexane/ethyl acetate 8/2) to provide 13.8 g of 2-trifluoromethanesulfonyloxy-8-(1-hydroxy-2-tert-butyldimethylsilyloxyethyl)quinoline in the form of a yellow oil. (Yield: 91%)

(8) 2-Trifluoromethanesulfonyloxy-8-(1-diethylamino-2-tert-butyldimethylsilyloxyethyl)quinoline 13.21 ml of triethylamine and 7 ml of methanesulfonyl chloride are successively added to a solution, cooled to 0° C. with an ice bath, of 13.8 g (30.53 mmol) of 2-trifluoromethanesulfonyloxy-8-(1'-hydroxy-2'-tert-butyldimethylsilyloxyethyl)quinoline in 300 ml of ethyl ether. The mixture is stirred for 30 min at 0° C. and then for 10 min at ambient temperature and is hydrolyzed by the addition of 300 ml of water. Extraction is carried out with ethyl acetate (3×250 ml). The organic phases are combined, dried over magnesium sulfate, filtered and concentrated under vacuum. The residue is dissolved in 200 ml of chloroform and 45 ml of diethylamine and the mixture is brought to reflux for 16 h. 200 ml of water are added and extraction is carried out with ethyl acetate (3×150 ml). The organic phases are combined, dried over magnesium sulfate, filtered and concentrated under vacuum. The residue is purified by silica chromatographic column (eluent: cyclohexane/ethyl acetate 8/2) to provide 14 g of 2-trifluoromethane sulfonyloxy-8-(1-diethylamino-2-tert-butyldimethylsilyloxyethyl) quinoline in the form of a yellow oil. (Yield: 90%)

(9) 2-Trifluoromethanesulfonyloxy-8-(1'-diethylamino-2'-hydroxyethyl)quinoline 0.94 g (1.85 mmol) of 2-trifluoromethanesulfonyloxy-8-(1-diethylamino-2-tert-butyldimethylsilyloxyethyl) quinoline, 14 ml of acetic acid, 5 ml of THF and 5 ml of water are placed in a 100 ml round-bottomed flask. The mixture is heated at 70° C. for 20 h, brought back to ambient temperature, hydrolyzed and brought to neutrality by addition of normal sodium hydroxide. Extraction is carried out with ethyl acetate and the organic phases are combined, dried over magnesium sulfate, filtered and concentrated under vacuum. The residue is purified by silica chromatographic column (eluent: dichloromethane/methanol 98/2) to provide 0.515 g of 2-trifluoro-methanesulfonyloxy-8-(1-diethylamino-2-hydroxyethyl)quinoline in the form of a yellow oil. (Yield: 71%)

(10) 2-Phenyl-8-(1-diethylamino-2-hydroxyethyl)quinoline 0.1 g (0.254 mmol) of 2-trifluoromethanesulfonyloxy-8-(1-diethylamino-2-hydroxyethyl)quinoline, 3 ml of toluene, 62 mg (0.51 mmol) of of phenylboronic acid, 53 mg (0.38 mmol) of potassium carbonate and 17.6 mg (0.0152 mmol) of tetrakis(triphenylphosphine)palladium are placed in a 20 ml three-necked flask. The mixture is heated with an oil bath at 90° C. for 2 h and 10 ml of water are added. Extraction is carried out with ethyl acetate and the organic phases are combined, dried over magnesium sulfate, filtered and concentrated under vacuum. The residue is purified by silica chromatographic column (eluent: dichloromethane/methanol 95/5) to provide 40 mg of 2-phenyl-8-(1-diethylamino-2-hydroxyethyl)quinoline in the form of a colorless oil. (Yield: 49%)

(11) 2-Phenyl-8-(1-diethylamino-2-hydroxyethyl)quinoline Pamoate

A solution of 43 mg (0.11 mmol) of pamoic acid in 1 ml of DMF is added to a solution of 40 mg (0.11 mmol) of 2-phenyl-8-(1-diethylamino-2-hydroxyethyl)quinoline in 1 ml of DMF. The solution is stirred for 15 min and then 10 ml of distilled water are added. The yellow precipitate obtained is filtered off, washed with 5×5 ml of distilled water and then dried in a desiccator under vacuum over phosphorus pentoxide to provide to provide 83 mg of 2-phenyl-8-(1-diethylamino-2-hydroxyethyl)quinoline pamoate in the form of a yellow solid; M.p.=120° C. (Quantitative yield)

EXAMPLE 4

By using essentially the same processes as those of the preceding examples, other compound of formula (I) in accordance with the invention was prepared. These compounds are those in the table below.

TABLE

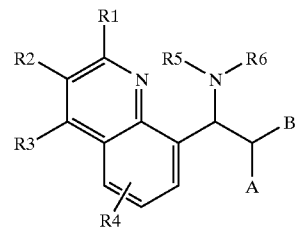

(I, D = H)

| No. | $R_1$ | $R_2$ | $R_3$ | $R_4$ | $R_5$ | $R_6$ | A | B | Salt | M.p. (° C.) |
|---|---|---|---|---|---|---|---|---|---|---|
| 1 | Ph | Me | H | H | Et | Et | OH | H | — | Oil |
| 2 | Ph | Me | H | H | Et | Et | OH | H | Pam | >215 |
| 2 | Ph | Me | H | H | Et | Et | OH | H | Pam | >215 |
| 3 R | Ph | Me | H | H | —CH((R)Me)-(CH$_2$)$_4$ | | OH | H | — | Wax |
| 4 R | Ph | Me | H | H | —CH((R)Me)-(CH$_2$)$_4$ | | OH | H | HCl | 68 |

TABLE-continued (I, D = H)

| No. | R₁ | R₂ | R₃ | R₄ | R₅ | R₆ | A | B | Salt | M.p. (° C.) |
|---|---|---|---|---|---|---|---|---|---|---|
| 5 S | Ph | Me | H | H | —CH((S)Me)-(CH₂)₄ | | OH | H | — | Wax |
| 6 S | Ph | Me | H | H | —CH((S)Me)-(CH₂)₄ | | OH | H | Pam | 158 |
| 7 S | Ph | Me | H | H | —CH((R)Me)-(CH₂)₄ | | OH | H | — | Wax |
| 8 S | Ph | Me | H | H | —CH((R)Me)-(CH₂)₄ | | OH | H | Pam | 164 |
| 9 R | Ph | Me | H | H | —CH((S)Me)-(CH₂)₄ | | OH | H | — | Wax |
| 10 R | Ph | Me | H | H | —CH((S)Me)-(CH₂)₄ | | OH | H | Pam | 125 |
| 11 | Ph(3-NO₂) | H | H | H | Et | Et | OH | H | — | Oil |
| 12 | Ph(3-NO₂) | H | H | H | Et | Et | OH | H | Pam | 105 |
| 13 | Ph(4-OMe) | H | H | H | Et | Et | OH | H | — | Oil |
| 14 | Ph(4-OMe) | H | H | H | Et | Et | OH | H | Pam | 110 |
| 15 | Ph(3-OMe) | H | H | H | Et | Et | OH | H | — | Oil |
| 16 | Ph(3-OMe) | H | H | H | Et | Et | OH | H | Pam | 120–126 |
| 17 | Ph | H | H | H | Et | Et | OH | H | — | Oil |
| 18 | Ph | H | H | H | Et | Et | OH | H | Pam | 120 |
| 19 | Ph(2-F) | H | H | H | Et | Et | OH | H | — | Oil |
| 20 | Ph(2-F) | H | H | H | Et | Et | OH | H | Pam | >250 |
| 21 | Ph(3-CF₃, 3'-CF₃) | H | H | H | Et | Et | OH | H | — | Oil |
| 22 | Ph(3-CF₃-3'-CF₃) | H | H | H | Et | Et | OH | H | Pam | 130–144 |
| 23 | Ph(3-Cl, 3'-Cl) | H | H | H | Et | Et | OH | H | — | Oil |
| 24 | Ph(3-Cl, 3'-Cl) | H | H | H | Et | Et | OH | H | Pam | 120–130 |
| 25 | Ph(4-CF₃) | H | H | H | Et | Et | OH | H | — | Oil |
| 26 | Ph(4-CF₃) | H | H | H | Et | Et | OH | H | Pam | 129–144 |
| 27 | Ph(3-CF₃) | H | H | H | Et | Et | OH | H | — | Oil |
| 28 | Ph(3-CF₃) | H | H | H | Et | Et | OH | H | Pam | 150–160 |
| 29 | Ph(2-CF₃) | H | H | H | Et | Et | OH | H | — | Oil |
| 30 | Ph(2-CF₃) | H | H | H | Et | Et | OH | H | Pam | 135–140 |
| 31 | Ph(3-NMe₂) | H | H | H | Et | Et | OH | H | — | Oil |
| 32 | Ph(3-NMe₂) | H | H | H | Et | Et | OH | H | Pam | 135–140 |
| 33 | Ph(3-NH₂) | H | H | H | Et | Et | OH | H | — | Oil |
| 34 | Ph(3-NH₂) | H | H | H | Et | Et | OH | H | Pam | 180 |
| 35 | Ph(2-OMe) | H | H | H | Et | Et | OH | H | — | Oil |
| 36 | Ph(2-OMe) | H | H | H | Et | Et | OH | H | Pam | 115 |
| 37 | Ph(4-F) | H | H | H | Et | Et | OH | H | — | Oil |
| 38 | Ph(4-F) | H | H | H | Et | Et | OH | H | Pam | 120–128 |
| 39 | Ph(3-F) | H | H | H | Et | Et | OH | H | — | Oil |
| 40 | Ph(3-F) | H | H | H | Et | Et | OH | H | Pam | 120–128 |
| 41 | Ph(3-F, 3'-F) | H | H | H | Et | Et | OH | H | — | oil |
| 42 | Ph(3-F, 3'-F) | H | H | H | Et | Et | OH | H | Pam | 120–125 |
| 43 | Ph(4-Me) | H | H | H | Et | Et | OH | H | — | Oil |
| 44 | Ph(4-Me) | H | H | H | Et | Et | OH | H | Pam | 120–135 |
| 45 | Ph(4-Ph) | H | H | H | Et | Et | OH | H | — | Oil |
| 46 | Ph(4-Ph) | H | H | H | Et | Et | OH | H | Pam | 135–140 |
| 47 | Ph(4-OCH₂-Ph) | H | H | H | Et | Et | OH | H | — | Oil |
| 48 | Ph(4-OCH₂Ph) | H | H | H | Et | Et | OH | H | Pam | 130–140 |
| 49 | 2-naphthalene | H | H | H | Et | Et | OH | H | — | Oil |
| 50 | 2-naphthalene | H | H | H | Et | Et | OH | H | Pam | 140–145 |
| 51 | Ph(2-F, 4-F) | H | H | H | Et | Et | OH | H | — | Oil |

TABLE-continued

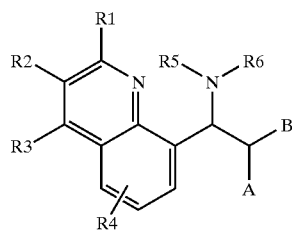

(I, D = H)

| No. | R₁ | R₂ | R₃ | R₄ | R₅ | R₆ | A | B | Salt | M.p. (° C.) |
|---|---|---|---|---|---|---|---|---|---|---|
| 52 | Ph(2-F, 4-F) | H | H | H | Et | Et | OH | H | Pam | 155 |
| 53 | Ph(3-OMe, 3'-OMe, 4-OMe) | H | H | H | Et | Et | OH | H | — | Oil |
| 54 | Ph(3-OMe, 3'-OMe, 4-OMe) | H | H | H | Et | Et | OH | H | Pam | 155 |
| 55 | 2-thiophene | H | H | H | Et | Et | OH | H | — | Oil |
| 56 | 2-thiophene | H | H | H | Et | Et | OH | H | Pam | 109–130 |
| 57 | 4-pyridine | H | H | H | Et | Et | OH | H | — | Oil |
| 58 | 4-pyridine | H | H | H | Et | Et | OH | H | Pam | 148–157 |
| 59 | Ph(2-OH) | H | H | H | Et | Et | OH | H | — | Oil |
| 60 | Ph(2-OH) | H | H | H | Et | Et | OH | H | Pam | 180–185 |
| 61 | Ph(2-Cl) | H | H | H | Et | Et | OH | H | — | Oil |
| 62 | Ph(2-Cl) | H | H | H | Et | Et | OH | H | Pam | 115–145 |
| 63 | Ph(2-NO₂) | H | H | H | Et | Et | OH | H | — | Oil |
| 64 | Ph(2-NO₂) | H | H | H | Et | Et | OH | H | Pam | 117–145 |
| 65 | Ph(2-NH₂) | H | H | H | Et | Et | OH | H | — | Oil |
| 66 | Ph(2-NH₂) | H | H | H | Et | Et | OH | H | Pam | 110–130 |
| 67 | Ph(2-C(O)CH₃) | H | H | H | Et | Et | OH | H | — | Oil |
| 68 | Ph(2-C(O)—CH₃) | H | H | H | Et | Et | OH | H | Pam | 115–130 |
| 69 | Ph(2-C(OH)—(CH₃)₂) | H | H | H | Et | Et | OH | H | — | Oil |
| 70 | Ph(2-C(OH)—(CH₃)₂) | H | H | H | Et | Et | OH | H | Pam | 120–140 |
| 71 | Ph(2-F) | Me | H | H | Et | Et | OH | H | — | Oil |
| 72 | Ph(2-F) | Me | H | H | Et | Et | OH | H | Pam | 120–145 |
| 73 | Ph(3-CF₃) | Me | H | H | Et | Et | OH | H | — | Oil |
| 74 | Ph(3-CF₃) | Me | H | H | Et | Et | OH | H | Pam | 160–170 |
| 75 | Ph(2-Cl) | Me | H | H | Et | Et | OH | H | — | Oil |
| 76 | Ph(2-Cl) | Me | H | H | Et | Et | OH | H | Pam | 130–140 |
| 77 | Ph(4-N₃) | H | H | H | Et | Et | OH | H | — | Oil |
| 78 | Ph(3-N₃) | Me | H | H | Et | Et | OH | H | — | Oil |
| 79 | Ph(2-N₃) | Me | H | H | Et | Et | OH | H | — | Oil |

In this table:
Pam represents a salt of pamoic acid,
HCl represents a hydrochloride,
"-" represents a compound in the free form,
Et represents an ethyl group,
Me represents a methyl group,
Ph represents a phenyl group.

Furthermore, the compounds for which the number is accompanied by an R are in the chiral form and of R stereochemistry for the benzyl carbon carrying the amine. The compounds for which the number is accompanied by an S are in the chiral form and of S stereochemistry for the benzyl carbon carrying the amine. If the amine, that is to say the NR₅R₆ group, exhibits a center of asymmetry, the absolute stereochemistry is specified in the table. All the other compounds in the table are racemates.

The compounds of the invention were subjected to biological tests intended to demonstrate their contractile activity on urethral and arterial smooth muscles.

1. The in vitro activity of the compounds of the invention was studied on urethral and arterial smooth muscles. These tests were carried out on female New Zealand rabbits weighing from 3 to 3.5 kg. The animals were killed by vertebral dislocation and then rings of tissue from the mesenteric arteries and from the urethra were removed. These rings of tissue were immersed in a modified Krebs solution oxygenated by a mixture of 95% $O_2$ and 5% $CO_2$. Each tissue sample was subjected to a tension of 1 g, phenylephrine was then introduced in cumulative doses and the dose/response curve was drawn up. After rinsing the samples, the compound to be studied was introduced in cumulative doses and the dose/response curve was drawn up. The contractile effect of each compound is evaluated by the calculation of the $pD_2$ (negative logarithm of the agonist concentration which induces 50% of the maximum contraction) and by the maximum effect representing the percentage of the maximum contraction obtained with phenylephrine (% $E_{max}$).

The results obtained show that the compounds in accordance with the invention exhibit:

a urethral $pD_2$ usually of between 4 and 8 an arterial $pD_2$ usually of less than 3, a urethral $\%E_{max}$ of more than 30, usually between 40 and 90, an arterial $\%E_{max}$ usually of less than 5.

2. The in vitro activity of the compounds of the invention were studied on the saphenous veins of the Yucatan miniature pig. The tissue is cut into a helix and is mounted in an isolated organ tank in a modified Krebs solution oxygenated by a mixture of 95% $O_2$ and 5% $CO_2$ held at 37 EC. The vessel is connected to an isometric sensor under a basal tension of 1 g and is connected to a polygraph which makes it possible to record variations in tension. The viability of each preparation is tested by prestimulation with 3 $\mu$M noradrenaline. After rinsing, the compound to be studied is introduced and its concentration/response curve constructed cumulatively until a maximum response is obtained. The contractile effect of each compound is evaluated by calculation of the $EC_{50}$ (concentration producing. 50% of the maximum response).

The compounds of the invention have made it possible to obtain a venoconstrictive activity with an $EC_{50}$ value usually of between 1 $\mu$M and 100 $\mu$M.

The compounds of the invention can be used in the treatment of venous insufficiency and of venous ulcers.

3. The in vivo activity of the compounds of the invention on blood and urethral pressure was studied in the amyelous rat and the rabbit, according to the following protocols:

Pithed Rats

Wistar rats are anesthetized and pithed (according to the technique described by Gillespie, MacLaren A. and Polock D., A method of stimulating different segments of the autonomic outflow from the spinal column to various organs in the pithed cat and rat; Br. J. Pharmacol., 1970, 40: 257–267).

Catheters are introduced via the femoral artery and a jugular vein. Another catheter is introduced into the urethra via an incision made in the bladder. The compounds to be tested are administered at increasing doses via intravenous infusion.

The results are expressed in doses ($\mu$g/kg) necessary to increase the urethral pressure by 10 cm of water ($UP_{10}$) or the arterial pressure by 10 mm of Hg ($AP_{10}$) or by 50 mm of Hg ($AP_{50}$).

The compounds of the invention, thus tested, made it possible to obtain:

a $UP_{10}$ with doses of less than 500 $\mu$g/kg, usually of between 5 and 200 $\mu$g/kg, an $AP_{10}$ with doses of greater than 600 $\mu$g/kg, usually of between 600 and 2 000 $\mu$g/kg, the $AP_{50}$ could not be reached.

Rabbits

The experiments are carried out on female New Zealand rabbits weighing between 3 and 4 kg anesthetized by a mixture of ketamine and xylazine. The catheters are introduced for the descending part of the aorta into the femoral artery, into a jugular vein and into the urethra (1.5 cm below the neck of the bladder).

The compounds to be tested are administered 5 to 15 days following the operation by intravenous (i.v.) administration over 5 minutes and in a single dose (of 10 or 100 $\mu$g/kg).

In this instance, the increase in the urethral pressure (UP) and in the arterial pressure (AP) were measured with respect to the urethral basal pressure and the arterial basal pressure respectively. The results obtained are expressed as percentage of premedication values at 5 minutes after intravenous (i.v.) administration.

The compounds of the invention, thus tested, made possible an increase in the UP of more than 50%, usually of between 50 and 350% after intravenous administration and usually of between 50 and 200% after force-feeding. The increase in the AP was always less than 10% and is usually 0%.

The combined results above show that the compounds of the invention have a strong urethral contractile action and a weak arterial contractile action.

They can be used as a medicament, in particular as an agent for contracting smooth muscles, and more particularly still in the treatment of urinary stress incontinence. In this indication, the compounds according to the invention are highly effective and usually exhibit fewer side effects than the medicaments conventionally used for such a treatment, in particular as regards side effects affecting the cardiovascular system, in particular the arterial beds.

The compounds according to the invention can also be employed in the treatment of venous insufficiencies, migraine or gastrointestinal disorders and as a vasoconstrictor for the mucous membrane of the nose.

The use of the compounds according to the invention for the preparation of medicaments intended for the treatment of the abovementioned pathologies forms an integral part of the invention.

According to another of its aspects, the present invention relates to pharmaceutical compositions including, as active principle, a compound according to the invention.

Thus, these pharmaceutical compositions comprise an effective dose of a compound according to the invention or of a pharmaceutically acceptable salt, solvate or hydrate of the latter and one or more suitable excipients.

Said excipients are chosen according to the pharmaceutical form and the method of administration desired.

In the pharmaceutical compositions of the present invention for oral, sublingual, subcutaneous, intramuscular, intravenous, topical, intratracheal, intranasal, transdermal or rectal administration, the active principles of formula (I) above or their optional salts, solvates or hydrates can be administered in unit administration forms, as a mixture with conventional pharmaceutical carriers, to animals or human beings for the prophylaxis or treatment of the above disorders or diseases. The appropriate unit administration forms comprise oral forms, such as tablets, gelatin capsules, powders, granules and oral solutions or suspensions, sublingual, buccal, intratracheal or intranasal administration forms, subcutaneous, intramuscular or intravenous administration forms, For topical application, the compounds according to the invention can be used in creams, ointments or lotions.

In order to obtain the desired prophylactic or therapeutic effect, the dose of active principle can vary between 0.1 $\mu$g and 50 mg per kg of body weight and per day. Although these dosages are average situation examples, there may be specific cases where higher or lower dosages are appropriate; such dosages also come within the invention. According to standard practice, the dosage appropriate to each patient is determined by the physician according to the method of administration, the weight of said patient and the response of said patient.

Each unit dose can comprise from 0.1 to 1 000 mg, preferably from 1 to 500 mg, of active ingredients in combination with a pharmaceutical carrier. This unit dose can be administered 1 to 5 times daily, so as to administer a daily dosage of 0.5 to 5 000 mg, preferably of 1 to 2 500 mg.

For example, when a solid composition is prepared in the form of tablets, the main active ingredient is mixed with a pharmaceutical vehicle, such as gelatin, starch, lactose, magnesium stearate, talc, gum arabic or the like. The tablets can be coated with sucrose, with a cellulose derivative or with other materials.

According to a second example, a preparation in gelatin capsules is obtained by mixing the active ingredient with a diluent and by pouring the mixture obtained into soft or hard gelatin capsules.

The present invention, according to another of its aspects, also relates to a method for the treatment of the above pathologies which comprises to administer a compound according to the invention.

What is claimed is:

1. A compound of formula (I)

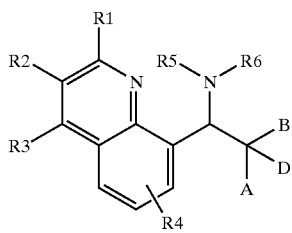

(I)

wherein:
- A represents a hydrogen atom, a hydroxyl, a $C_{1-3}$ alkoxy group, a hydroxy($C_{1-6}$ alkyl) group, a ($C_{1-3}$ alkoxy)($C_{1-3}$ alkyl) group, a thiol, ($C_{1-6}$ alkyl)sulfanyl or a halogen;
- B and D represent, independently of one another, a hydrogen atom, a $C_{1-6}$ alkyl group, a fluoro($C_{1-6}$ alkyl) group or a perfluoro($C_{1-2}$ alkyl) group or B and D together from an oxo;
- $R_1$ represents a phenyl, a naphthyl or a heteroaryl comprising 4 or 5 carbon atoms and, as heteroatom, an oxygen, a sulfur or a nitrogen; it being possible for the phenyl, the naphthyl or the heteroaryl to be substituted by one, two or three substituents chosen from the group consisting of a halogen, a hydroxyl, a nitro, an amino, an azido, a $C_{1-6}$ alkyl group, a hydroxy($C_{1-6}$ alkyl) group, a ($C_{1-6}$ alkyl)carbonyl group, a ($C_{1-6}$ alkyl)amino group, a di($C_{1-6}$ alkyl)amino group, a fluoro($C_{1-6}$ alkyl) group, a perfluoro($C_{1-2}$ alkyl) group, a $C_{1-6}$ alkoxy group, a phenyl, a benzyl, and a benzyloxy;
- $R_2$ and $R_3$ represent, independently of one another, a hydrogen atom, a halogen or a $C_{1-6}$ alkyl group,
- $R_4$ represents a hydrogen atom, a hydroxyl or a halogen, and
- $R_5$ and R6 represent, independently of one another, a hydrogen atom, a $C_{1-6}$ alkyl group, a $C_{2-6}$ alkenyl group, a $C_{3-6}$ cycloalkyl group, a $C_{3-6}$ cycloalkenyl group, a fluoro($C_{1-6}$ alkyl) group or a perfluoro($C_{1-2}$ alkyl) group or $R_5$ and $R_6$ together form a $C_{2-6}$ alkylene chain or a $C_{3-6}$ alkenylene chain, to give, with the nitrogen to which they are attached, a heterocycle, this heterocycle optionally being substituted by a $C_{1-4}$ alkyl group;

or an acid-addition salt thereof.

2. A compound according to claim 1 wherein:
A represents a hydrogen, hydroxyl, a thiol or a halogen;

B and D represent a hydrogen atom;

$R_1$ represents a phenyl, a naphthyl or a heteroaryl comprising 4 or 5 carbon atoms and, as heteroatom, a sulfur or a nitrogen, it being possible for the phenyl, the naphthyl or the heteroaryl to be substituted by one, two or three substituents chosen from the group consisting of a halogen, a hydroxyl, a nitro, an amino, an azido, a $C_{1-3}$ alkyl group, a hydroxy($C_{1-3}$ alkyl) group, a ($C_{1-3}$ alkyl)carbonyl group, a ($C_{1-3}$ alkyl)amino group, a di($C_{1-3}$ alkyl)amino group, a fluoro($C_{1-6}$ alkyl) group, a perfluoro($C_{1-2}$ alkyl) group, a $C_{1-3}$ alkoxy group, a phenyl, a benzyl and a benzyloxy;

$R_2$ and $R_3$ represent, independently of one another, a hydrogen atom or a $C_{1-6}$ alkyl group;

$R_5$ and $R_6$ represent, independently of one another, a hydrogen atom or a $C_{1-6}$ alkyl group or $R_5$ and $R_6$ together form a $C_{2-6}$ alkylene chain, to give, with the nitrogen to which they are attached, a heterocycle chosen from a piperidyl, azetidinyl or pyrrolidyl, this heterocycle optionally being substituted by a $C_{1-4}$ alkyl group.

3. A compound according to claim 1 wherein:
A represents a hydroxyl;
B and D and $R_4$ represent a hydrogen atom;
$R_1$ represents a naphthyl, a thiophene, a pyridine or a phenyl, it being possible for the phenyl to be substituted by one, two or three substituents chosen from the group consisting of a a halogen, a hydroxyl, a nitro, an amino, an azido, a $C_{1-3}$ alkyl group, a hydroxy($C_{1-3}$ alkyl) group, a ($C_{1-3}$ alkyl)carbonyl group, a ($C_{1-3}$ dialkyl) amino group, a perfluoro($C_{1-2}$ alkyl) group, a $C_{1-3}$ alkoxy group, a phenyl and a benzyloxy;
$R_2$ and $R_3$ represent, independently of one another, a hydrogen atom or a $C_{1-3}$ alkyl group; and
$R_5$ and $R_6$ represent, independently of one another, a $C_{1-3}$ alkyl group or $R_5$ and $R_6$, together with the nitrogen to which they are attached, a piperidyl, this piperidyl optionally being substituted a $C_{1-2}$ alkyl group.

4. A compound according to claim 1 selected from the group consisting of:
2-Phenyl-3-methyl-8-(1-diethylamino-2-hydroxyethyl) quinoline,
2-Phenyl-3-methyl-8-(1-(R)-[2'-(R)methylpiperidino]-2-hydroxyethyl)quinoline,
2-Phenyl-8-(1-diethylamino-2-hydroxyethyl)quinoline,
2-Thiophen-2-yl-8-(1-diethylamino-2-hydroxyethyl) quinoline,
2-(2-Fluorophenyl)-3-methyl-8-(1-diethylamino-2-hydroxyethyl)quinoline,
and acid-addition salts thereof.

5. A compound of formula (III):

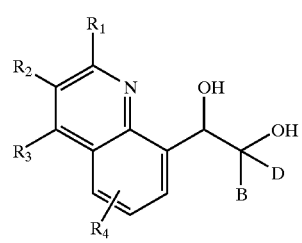

III wherein $R_1$, $R_2$, $R_3$, $R_4$, B and D have the meanings given in claim 1.

6. A process for the preparation of a compound according to claim 1 in which A represents a hydroxyl group which comprises protecting the hydroxyl group geminal to the B group of the compound of formula III:

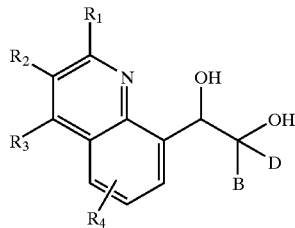

III to give the compound of formula II

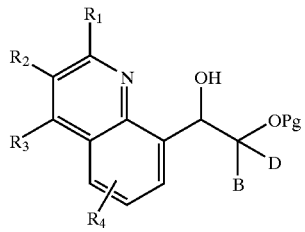

II in which Pg represents a protective group, reacting the compound of formula II, after an optional activation of the hydroxyl group, with an amine $NHR_5R_6$; and deprotecting the compound thus obtained to give the compound of formula (I) wherein $R_1, R_2, R_3, R_4, R_5, R_6$, D and B have the meanings given in claim 1.

7. A pharmaceutical composition comprising a compound according to claim 1 and a pharmaceutically acceptable excipient.

8. A pharmaceutical composition comprising a compound according to claim 2 and a pharmaceutically acceptable excipient.

9. A pharmaceutical composition comprising a compound according to claim 3 and a pharmaceutically acceptable excipient.

10. A pharmaceutical composition comprising a compound according to claim 4 and a pharmaceutically acceptable excipient.

11. A method for the treatment of urinary incontinence, venous insufficiency, migraine or gastrointestinal disorders which comprises administering to a patient in need of such treatment a therapeutically effective amount of a compound according to claim 1.

12. A method for the treatment of urinary incontinence, venous insufficiency, migraine or gastrointestinal disorders which comprises administering to a patient in need of such treatment a therapeutically effective amount of a compound according to claim 2.

13. A method for the treatment of urinary incontinence, venous insufficiency, migraine or gastrointestinal disorders which comprises administering to a patient in need of such treatment a therapeutically effective amount of a compound according to claim 3.

14. A method for the treatment of urinary incontinence, venous insufficiency, migraine or gastrointestinal disorders which comprises administering to a patient in need of such treatment a therapeutically effective amount of a compound according to claim 4.

15. A method according to claim 11 for the treatment of urinary incontinence.

16. A method according to claim 12 for the treatment of urinary incontinence.

17. A method according to claim 13 for the treatment of urinary incontinence.

18. A method according to claim 14 for the treatment of urinary incontinence.

* * * * *